United States Patent [19]

Fischer et al.

[11] Patent Number: 4,562,252

[45] Date of Patent: Dec. 31, 1985

[54] PROCESS FOR ISOLATING MICROBIAL POLYSACCHARIDES FROM THEIR AMINE ADDUCTS

[75] Inventors: Edgar Fischer, Frankfurt am Main; Merten Schlingmann, Königstein, both of Fed. Rep. of Germany

[73] Assignee: Hoechst Aktiengesellschaft, Fed. Rep. of Germany

[21] Appl. No.: 522,611

[22] Filed: Aug. 12, 1983

[30] Foreign Application Priority Data

Aug. 14, 1982 [DE] Fed. Rep. of Germany ....... 3230302

[51] Int. Cl.$^4$ .......................... C07H 1/06; C08B 37/00
[52] U.S. Cl. ...................................... 536/114; 536/127
[58] Field of Search ................................. 536/114, 127

[56] References Cited

U.S. PATENT DOCUMENTS

| 3,422,085 | 1/1969 | Gill et al. | 536/114 |
| 3,598,730 | 8/1971 | Nordgren et al. | 536/114 |
| 3,729,460 | 4/1973 | Patton | 536/114 |
| 3,928,316 | 12/1975 | Jordan et al. | 536/114 |

Primary Examiner—Johnnie R. Brown
Attorney, Agent, or Firm—Finnegan, Henderson, Farabow, Garrett & Dunner

[57] ABSTRACT

Microbial polysaccharides can be liberated from their amine adducts by treating them with ammonia or a highly volatile amine in the presence of monohydric alkanols having 1 to 3 carbon atoms. It is advantageous to use the amine adduct in the form of a moist press cake in which it is isolated from fermenter broths. The free polysaccharides are obtained in a virtually quantitative yield.

10 Claims, No Drawings

PROCESS FOR ISOLATING MICROBIAL POLYSACCHARIDES FROM THEIR AMINE ADDUCTS

The invention relates to a process for isolating microbial polysaccharides from their adducts with amines.

Owing to their excellent properties, fermentation-produced extracellular microbial polysaccharides are used in industry as thickeners, gelling or suspending agents, protective colloids or water-binding agents. Their method of preparation makes these products fairly expensive, one contributing factor to their high price being the existing, technically complicated methods of isolating them.

U.S. Pat. No. 3,928,316, discloses the isolation of the anionic heteropolysaccharide obtained by fermentation with the aid of the bacterium Xanthomonas campestris NRRL B-1459 in the form of a water-insoluble salt of a primary long-chain amine from the acidified dilute fermentation solutions. If it is intended to cleave this salt, this is done with alcoholic potassium hydroxide solution, giving the potassium salt, which, however, still contains amine.

The published British patent application 2,053,945 describes a similar process where a polyamine is used to precipitate the polysaccharide. In the event that it is intended to isolate the amine from the amine salt, this patent application gives a method whereby the dry salt is treated with a solution of a strong base in a liquid which does not dissolve the free acidic polysaccharide, such as aqueous methanol.

Patent application Ser. No. 522,608 of the same date (German Patent Application P 32 30 303.3) relates to a process for isolating microbial polysaccharides from their aqueous solutions by precipitating them in an acidic medium in the form of an adduct with a long-chain alkylamine, which comprises using an amine of the formula $$NR^1R^2R^3$$

in which $R^1$ is alkyl having 10–20 carbon atoms, and $R^2$ and $R^3$, which are identical or different, denote methyl or ethyl.

The known methods of cleaving the amine adducts do not proceed in some cases to completion, and lead to salt-containing polymers, so that it is necessary to carry out further purification operations, which are technically complicated because of the treatment of the effluent. The treatment of the adducts with strong alkalis can also damage the polymer.

We have now found a process for isolating microbial polysaccharides from their amine adducts by treating them with alkaline agents in the presence of monohydric alkanols having 1 to 3 carbon atoms, which comprises using ammonia or a highly volatile amine as the alkaline agent.

Below, preferred embodiments of the invention will be illustrated in more detail:

Preferable starting materials are those adducts which are derived from xanthan as the microbial polysaccharide and a primary or tertiary fatty alkylamine (having two short-chain alkyl radicals). These adducts are advantageously used in the moist state, for example in the form of a press cake, in which they are obtained in the course of isolating the microbial polysaccharides from the fermentation solutions. The drying of the adducts, which not only requires considerable amounts of energy but also can impair the solubility and swelling properties of the adducts, is thus dispensed with. The small amounts of water which are introduced when moist adducts are used do not interfere with the process according to the invention.

The alkanols used are advantageously of the commercially available technical grade. The small amounts of water the products contain have no adverse influence on the process according to the invention. However, sizeable amounts of water are not advantageous, since the free microbial polysaccharides, in particular xanthan, are soluble in water but insoluble in the lower alkanols. A relatively high water content, in general above 30%, relative to the weight of the alcohol, could thus present a problem in the working-up. If too much water is introduced into this system with the moist adduct or with the amine, (the permissible upper limit depending on the polysaccharide, the alcohol and the amine), correspondingly more alcohol should be used.

If ammonia is the alkaline agent used, it is advantageously used in the form of a solution of the lower alkanol, in particular in the form of a saturated solution. Since ammonia, like the primary and secondary amines, can react with reactive groups, in particular ester groups, of the microbial polysaccharides, the process is preferably carried out at low to moderately elevated temperatures if ammonia is used. This also dispenses with the need to operate under pressure.

In contrast, if tertiary amines, and adducts of tertiary amines, are used, it is possible to work at elevated temperatures without damaging the product. On the one hand, elevated temperatures shorten the time the process takes, but, on the other hand, temperatures in the vicinity of the boiling point of the amine or of the alcohol necessitate more complicated apparatus. For this reason, one will in practice select a temperature which suits the available apparatus and which is easily determined in simple preliminary experiments.

For the purposes of the invention, highly volatile amines are primarily those which have a boiling point of less than 150° C. under normal pressure. Amines having a higher boiling point are less convenient, since these amines are more difficult to regenerate by distillation. It can also be difficult to separate the product from the amines liberated from the adducts. For this reason it is preferable to use primary alkylamines having an alkyl radical of up to 6 carbon atoms, secondary amines having identical or different alkyl radicals of up to 4 carbon atoms and tertiary amines having identical or different alkyl radicals of up to 3 carbon atoms. Trimethylamine, triethylamine, dimethylethylamine and diethylmethylamine are particularly preferable. These amines are likewise advantageously used in the form of their solutions of the alkanol used.

The choice of the alkaline agent also has an effect on the chemical nature of the product: due to the high volatility, even an excess of ammonia can be easily and rapidly removed on drying the liberated polysaccharide.

If an amine-free product is desired, ammonia is preferable. Higher-boiling amines are preferable when the process according to the invention is designed in the form of a warm extraction method or a distillation method, especially if such methods are carried out on a continuous basis.

The weight ratio of alcohol to amine or ammonia vary within wide limits, but it is advantageously about 1:10 to about 100:1. Since some adducts become highly solvated in alcohols, and form a gel, it is advantageous to use from the start a sufficiently concentrated alcoholic solution of ammonia or of the amine, since the extent of solvation is supressed in these solutions. Nor is the liberated polysaccharide solvated in these solutions. Instead, it precipitates in the form of an easily separated precipitate.

Since the process is carried out in a heterogeneous system, it is advisable to use apparatus which can exert a stirring, cutting, kneading, shearing or milling action on the solid.

The microbial polysaccharides are obtained in an easily separable form, and, when they have dried, they are largely in the form of the free acid. The products are distinguished by very favorable viscosity properties.

The liquid phase, which consists of the alcohol, the amine used as the alkaline agent and the liberated amine, can easily be worked up by distillation. The amine liberated from the adduct can immediately be used again to separate microbial polysaccharides from their fermentation solutions. That mixture of alcohol and highly volatile amine which passes over can be returned into the process. The choice of an amine having a suitable boiling point permits a completely continuous design of the process.

In the Examples which follow, parts and percentages are by weight, unless otherwise indicated. Parts by volume relate to parts by weight as the liter relates to the kg.

First, we shall describe a method which has not been reported in the literature, whereby an adduct is prepared from xanthan and a tertiary fatty alkylamine (German patent application P 32 30 303.3):

The production strain used was Xanthomonas campestris NRRL B-1459. An agar culture in a glucose/peptone medium was transferred to the initial culture, and incubated therein at 30° C. in a shaker. This culture was used as the inoculum (3%) for a 10 liter fermenter the nutrient medium of which contained 3-5% of glucose or sucrose, 0.15-0.25% of cornsteep, 0.1 to 0.2% of sodium nitrate, 0.1% of dipotassium phosphate and 0.05% of magnesium sulfate hydrate. The inoculated fermenter was kept at 28° C., and aerated with stirring (400 rpm) at a rate of 10 liters of air/min. After about 36 hours, the fermentation medium contained 18-20 g of xanthan per liter.

0.85 g of tallowalkyldimethylamine (carbon chain distribution in the tallowalkyl radical: about 5% of $C_{14}$; 30% of $C_{16}$; and 65% of $C_{18}$) was stirred into 100 g of a xanthan solution having a polysaccharide content of 1.8%. 2.5 g of 2N acetic acid was added, the dispersion obtained was coagulated, and the product was precipitated in the form of initially markedly swollen flat cakes which rapidly became dissolvated on further stirring. The adduct was filtered off, and washed with deionized water, and the water was removed by pressing. This gave 6.2 g of a moist press cake which contained 1.8 g of xanthan and 0.43 of amine.

EXAMPLE 1

100 parts of moist press cake consisting of an adduct of tallowalkylamine on xanthan, which contained 32% of xanthan, were disintegrated in a mixer which was equipped with a rotary cutter and held 6,000 parts of methanol which contained 1.5% of ammonia. The short fibers of xanthan liberated in this process were filtered off and washed with methanol until the methanol running off gave a neutral reaction. The filter cake was dried and comminuted. The xanthan was obtained virtually quantitatively (31.8 parts). The product was completely soluble in deionized water. The methanolic mother liquors could be used for several batches without having to be worked up in between.

EXAMPLE 2

Example 1 was repeated, except that a moist press cake or an adduct of tallowalkyldimethylamine and xanthan was used. The virtually quantitatively obtained xanthan dissolved completely in deionized water.

EXAMPLE 3

10 parts of a moist press cake consisting of the adduct of lauryldimethylamine and xanthan, and containing 36% of xanthan, were disintegrated in a mixer containing 150 parts of a mixture of 2 parts per volume of isopropyl alcohol and 1 part per volume of triethylamine. The resulting suspension was continually extracted in a hot extractor by means of the same mixture of isopropyl alcohol and amine. The cleavage had ended after about 3 hours. A sample of the extracted material was completely soluble in deionized water, and, when it had dried, exhibited the properties characteristic of free xanthan.

We claim:

1. In a process for cleaving amine adducts of polysaccharides and for isolating the free microbial polysaccharides from said amine adducts by treating said adducts with alkaline agents in the presence of monohydric alkanols having 1 to 3 carbon atoms, the improvement comprising using ammonia or a highly volatile amine capable of cleaving said free polysaccharide from said amine adduct as the alkaline agent.

2. The process as claimed in claim 1, wherein the ammonia or the amine is used in the form of a solution of the alkanol.

3. The process as claimed in claim 1, wherein an amine is used which has a boiling point of less than 150° C. under normal pressure.

4. The process as claimed in claim 1, wherein a tertiary amine is used as the highly volatile amine.

5. The process as claimed in claim 1, wherein the weight ratio of alcohol to amine or ammonia is 1:10 to 100:1.

6. The process as claimed in claim 1, wherein the amine adduct is used in the form of a moist press cake.

7. The process as claimed in claim 1, wherein the microbial polysaccharide is xanthan.

8. The process as claimed in claim 1, wherein the amine in the adduct is a primary fatty alkylamine.

9. The process as claimed in claim 1, wherein the amine in the adduct is a tertiary fatty alkylamine having two short-chain alkyl radicals.

10. The process as claimed in claim 1 which is carried out without applied pressure at a temperature below the boiling point of the reaction mixture.

* * * * *